US00PP08625P

United States Patent [19]

De Meyer

[11] Patent Number: Plant 8,625

[45] Date of Patent: Mar. 1, 1994

[54] GUZMANIA PLANT NAMED ZENITH

[75] Inventor: Henri De Meyer, Destelbergen, Belgium

[73] Assignee: H. De Meyer-De Rouck, Laarne, Belgium

[21] Appl. No.: 34,758

[22] Filed: Mar. 18, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new and distinct cultivar of Guzmania plant named Zenith, characterized by its shiny red bracts before flowering turning to a deep red after flowering; the tips of the uppermost bracts can vary in color to a much darker greyed-purple or black-red whereas the bottom bracts have a green tip and a grey-green-red zone which is a link to the red colored lower half; lower leaves which are primarily dark green in color and which provide excellent contrast with the flower cone; purplish striped leaf sheaths, and its long lasting inflorescence.

2 Drawing Sheets

The present invention comprises a new and distinct cultivar of *Guzmania squarrosa*, referred to by the cultivar name Zenith. The genus Guzmania is within the family Bromeliaceae.

Bromeliaceae is a very large family comprised of approximately 50 genera and over 1000 species. Methods of hybridization, germination of seed and asexual propagation of species within the family are well known in the art and are described in Benzing, David H., *The Biology of the Bromeliads*, Mad River Press (1980); Rauh, W., *Bromelien*, Eugen Ulmer Stuttgart (1987); and Zimmer, K., *Bromelien*, Paul Parey (1986), each of which is incorporated by reference herein.

Zenith is a product of a planned breeding program conducted in Laarne, Belgium. The program evolved from the importation by the inventor of seeds of several different cultivars of *Guzmania squarrosa* from Ecuador. When grown out to flower, several plants were selected for their beautiful flowers, and were subsequently crossed with cultivars of the species *Guzmania minor*.

Zenith was originated by the inventor Henri De Meyer from a hybridization made in the program in Laarne, Belgium. The female parent was an unnamed *Guzmania minor* cultivar identified as "red". The male parent of Zenith was an unnamed *Guzmania squarrosa* cultivar.

Zenith was discovered and selected by the inventor after flowering in late 1990. The new cultivar was thereafter asexually reproduced from offshoots under the supervision of the inventor in a controlled environment in Laarne, Belgium. The offshoots can be rooted with the resulting plantlets being detached from the mother plant and potted up in an appropriate growing mixture.

Horticultural examination of plants so propagated has demonstrated that the combination of characteristics as herein disclosed for Zenith are firmly fixed and retained through successive generations of asexual reproduction, which can be effected by offshoots as described, or by known tissue culture techniques.

Zenith has not been observed under all possible environmental conditions. The phenotype may vary significantly when grown under different conditions of temperature, light, and other determining factors, without, however, any variation in genotype. The following observations, measurements and comparisons describe plants grown in Laarne, Belgium under greenhouse conditions which approximate those generally used in commercial practice.

The following traits have been repeatedly observed and are determined to be basic characteristics of Zenith which in combination distinguish this Guzmania as a new and distinct cultivar:

1. The bracts of Zenith are bright deep red in base color, varying to a black-red at the top, whereas the bottom bracts have a green top and a grey-green-red zone which is the link to the red colored lower half. With younger leaves this greyish zone gradually moves up to the top.

2. The lower leaves are primarily dark green in color and provide excellent contrast with the sturdy flower cone.

3. The inflorescence is long lasting.

4. The fully grown leaf sheaths are well formed and closely linked at the base. The leaf sheaths have a purplish striped pattern. The stripes are so close together on the sheath's leaf blade that it looks as if the color of the leaf sheath is purple with only a few fine green stripes.

The accompanying photographic drawings show the inflorescence and foliage characteristics of Zenith as clearly as possible. The photo on the first sheet comprises a top perspective view of a substantial part of a plant of Zenith in bloom. The photo on the second sheet comprises a top view showing the inflorescence in more detail. The colors are as nearly true as possible with illustrations of this type.

Zenith can be compared in certain respects to the commercially available cultivar Denise. Zenith and Denise have the same green foliage color, but Zenith is a little smaller in growth habit. Zenith is further distinguished from Denise by its darker red bracts and its thicker and shorter flower stem.

In the following description, color references are made to The Royal Horticultural Society Colour Chart. The color values were determined at Laarne, Belgium.

Classification:

*Botanical*.—*Guzmania squarrosa* cv. Zenith.

PLANT

Form: Rosette.

Height: About 38 cm when plant is in bloom. The leaf rosette has a height of about 30 cm.

Diameter: Approximately 80–90 cm when plant is in bloom.

Growth habit: Stemless.

Method of propagation: By offshoots or tissue culture.

Foliage:

*Quantity.*—Some 20 to 22 leaves form a close rosette of which the bottom leaves have a length of 40 to 50 cm.

*Size.*—The bottom leaves have a width of about 3 to 3.5 cm and the fully grown top leaves have a width of about 4 to 5.5 cm.

*Shape.*—Linear with a pointed tip; leaf edge is entire and upright.

*Surface texture.*—The leaf surface is ribbed and shiny, both top and bottom surfaces.

*Color.*—The top surface is approximately 147A and the bottom surface is approximately 148A with a fine purple pattern.

*Leaf sheaths.*—Well formed and closely linked at the base, having a length of 9–14 cm up to the narrowing, and a width of 4–9 cm. They bear purple stripes approximately 187A-B, with the stripes being so close together on the sheath's leaf blade that it looks as if the leaf sheath's color is purple (187A-B), with only a few fine green stripes.

BRACTS

Quantity: Approximately 25 bracts are regularly spread along the length of the flower shaft, completely surrounding the shaft.

Size: Bracts at the bottom of the flower shaft have a length of about 40 cm and a width of 5 cm, slightly narrowing. The bracts near the top of the flower shaft have a length of 10 to 20 cm and a width of approximately 5 cm, slightly narrowing and ending in a tip.

Shape: At approximately one-third of the length of the bracts, the leaf blade curls outwards.

Color: The bracts at the top of the flower shaft are a generally shiny red (44A) before flowering, turning to a deep red color (46B) after flowering. The tips of the uppermost bracts can vary in color to a much darker greyed-purple or reddish black 187A, whereas the bottom bracts have a green tip (147A) and a grey-green-red zone which is the link to the red colored lower half. With younger leaves this greyish zone gradually moves up to the top.

FLOWERS

Borne: Some 15 headlike subflower systems are embedded, each separately, in the axils of one of the top bracts.

Blooming habit: Flowers bloom approximately 16 weeks after induction. Single flowers bloom only one day, and total inflorescence (from the first to last flower) lasts approximately eight (8) weeks.

Quantity: About 14 single flowers in each subflower system.

Size: The entire flower system (all subflowers together), which is part of the inflorescence, has a length of approximately 12 cm and a diameter of 6 cm. Each subflower system typically has a length of 4 to 4.5 cm and a width of 2.5 to 3 cm, and each individual flower is about 4 to 4.5 cm in length.

Shape: Straight in the subflower system.

Color: The bract of each flower has a red transparent color at the top half and a transparent white at the bottom.

Sepals: Three in number, fasciated at the base and membranous (4C). The sepals have a length of approximately 2 cm and a width of approximately 3 mm.

Petals: There are three, fasciated with each other and with the 6 stamens. The petals have a length of approximately 2.5 cm and a width of approximately 4 mm. The petal color is 12A.

Seed capsule: A reddish brown pyxidium of about 3 cm is formed.

Reproductive organs: There is one pistil and 6 stamens; typical in shape and color.

I claim:

1. A new and distinct cultivar of Guzmania plant named Zenith, as illustrated and described.

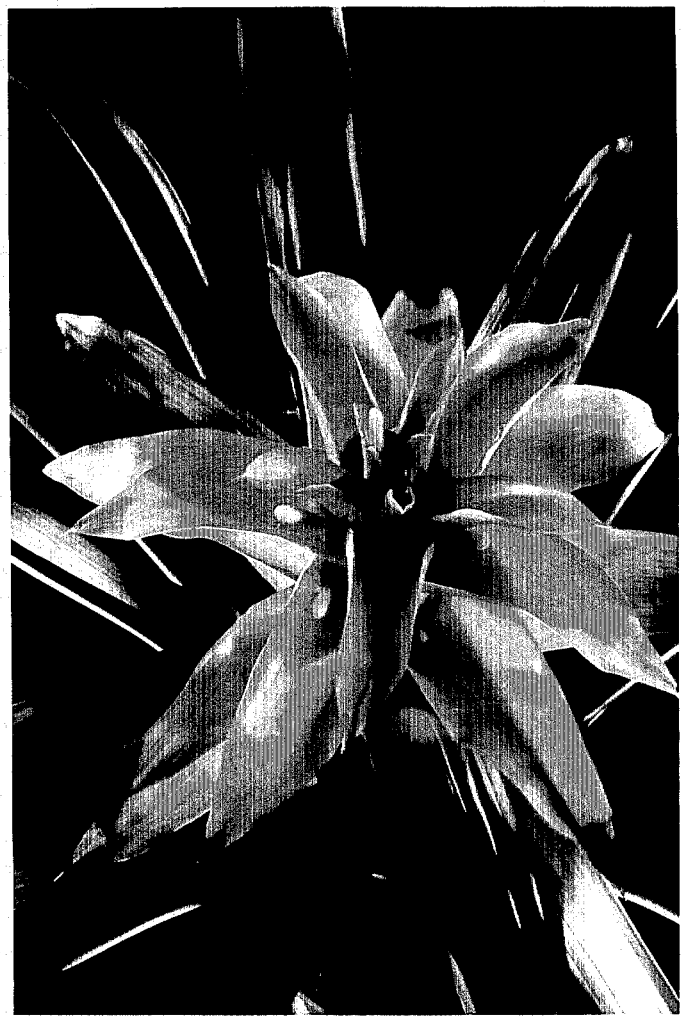

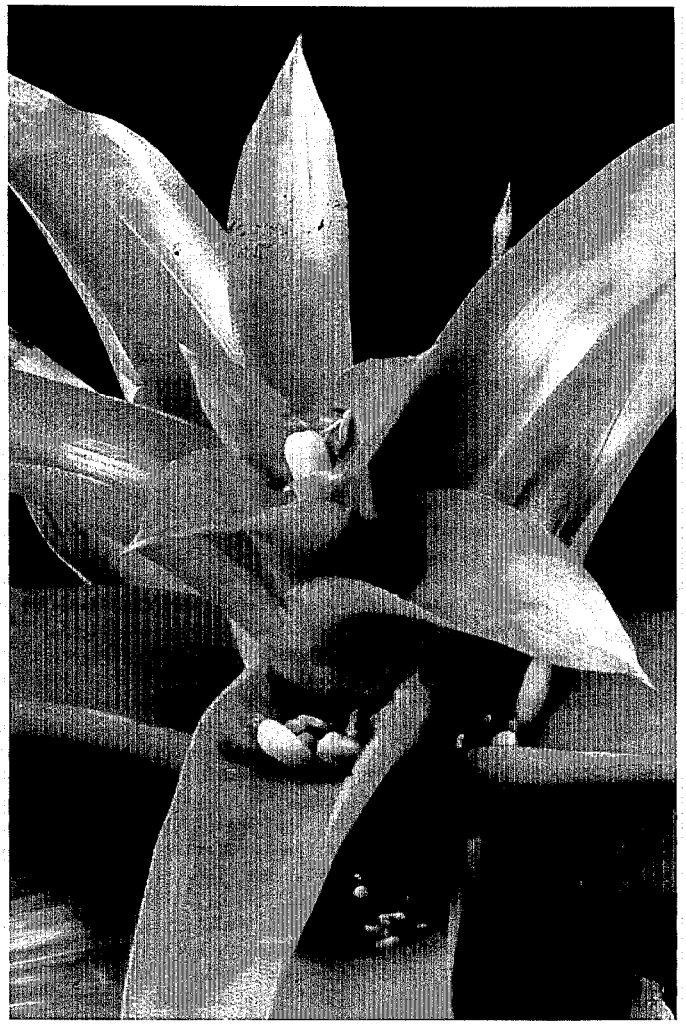

* * * * *